(12) United States Patent
Hultgren

(10) Patent No.: US 6,206,693 B1
(45) Date of Patent: Mar. 27, 2001

(54) BUCCAL IMPRESSION REGISTRATION APPARATUS, AND METHOD OF USE

(75) Inventor: Bruce Willard Hultgren, Victoria, MN (US)

(73) Assignee: Iris Development Corporation, Eden Prairie, MN (US)

( * ) Notice: Subject to any disclaimer, the term of this patent is extended or adjusted under 35 U.S.C. 154(b) by 0 days.

(21) Appl. No.: 09/311,436

(22) Filed: May 14, 1999

Related U.S. Application Data

(63) Continuation-in-part of application No. 08/789,918, filed on Jan. 28, 1997, now abandoned.

(51) Int. Cl.⁷ ............................................. A61C 9/00
(52) U.S. Cl. ................................................ 433/38; 433/37
(58) Field of Search ................................. 433/37, 38, 41, 433/45, 47, 215

(56) References Cited

U.S. PATENT DOCUMENTS

| | | |
|---|---|---|
| 2,933,811 * | 4/1960 | Lifton . |
| 4,182,312 | 1/1980 | Mushabac . |
| 4,449,927 | 5/1984 | Taylor et al. . |
| 4,602,905 | 7/1986 | O'Keefe, III . |
| 4,611,288 | 9/1986 | Duret et al. . |
| 4,752,964 | 6/1988 | Okada et al. . |
| 4,827,909 | 5/1989 | Kato et al. . |
| 4,935,635 | 6/1990 | O'Harra . |
| 5,017,139 | 5/1991 | Mushabac . |
| 5,027,281 | 6/1991 | Rekow et al. . |
| 5,071,252 | 12/1991 | Matsuura . |
| 5,102,335 | 4/1992 | Getz . |
| 5,121,333 | 6/1992 | Riley et al. . |

(List continued on next page.)

FOREIGN PATENT DOCUMENTS

WO 91/02458 10/1991 (WO) .

OTHER PUBLICATIONS

"Digital Record Keeping", http://www.webworldinc.com/orthovision/RecordsBrochure.htm (Jul. 31, 1996).
"Ortho–Vision Technologies", http://www.webworldinc.com/orthovision/News1Q96.htm (Jul. 31, 1996).
"OTP for Windows", http://www.webworldinc.com/orthovision/OTP Brochure.htm (Jul. 31, 1996).
"Treat Your Patients With Care", http://www.sibworldinc.com/orthovision/treatwithcare.htm (Jul. 31, 1996).
"Welcome to Ortho–Vision", http://www.webworldinc.com/orthovision/ (Jul. 31, 1996).

*Primary Examiner*—Ralph A. Lewis
(74) *Attorney, Agent, or Firm*—Merchant & Gould PC

(57) ABSTRACT

An apparatus and method for forming dental impressions to record the bite registration of a patient's teeth. In accordance with the present invention, an impression is taken of a predetermined set of teeth on each side of the patient's mouth in the buccal region thereof to record the bite registration of the upper and lower teeth. The impression is preferably formed by a buccal impression apparatus which includes a rigid frame member having first and second arms and a central section interconnected therebetween, with the frame member defining an open area. A mesh material is connected between the first and second arms and the central section within the open area. The mesh material permits a moldable material to adhere to the frame member during the formation of the impression, with the frame member supporting the moldable material and providing a means to support the impression upon a scanning apparatus. The buccal apparatus has a length such that it extends over a predetermined set of teeth on one side of the patient's mouth. In this manner, only a partial impression of the bite registration is recorded.

17 Claims, 10 Drawing Sheets

U.S. PATENT DOCUMENTS

| | | |
|---|---|---|
| 5,121,334 | 6/1992 | Riley et al. . |
| 5,124,524 | 6/1992 | Schuster et al. . |
| 5,128,870 | 7/1992 | Erdman et al. . |
| 5,173,048 | 12/1992 | Summer . |
| 5,184,306 | 2/1993 | Erdman et al. . |
| 5,198,877 | 3/1993 | Schulz . |
| 5,224,049 | 6/1993 | Mushabac . |
| 5,257,184 | 10/1993 | Mushabac . |
| 5,257,203 | 10/1993 | Riley et al. . |
| 5,273,429 | 12/1993 | Rekow et al. . |
| 5,316,474 * | 5/1994 | Robertson ............................... 433/37 |
| 5,338,198 | 8/1994 | Wu et al. . |
| 5,343,391 | 8/1994 | Mushabac . |
| 5,346,395 | 9/1994 | Adell . |
| 5,347,454 | 9/1994 | Mushabac . |
| 5,348,474 | 9/1994 | Pasini . |
| 5,370,533 * | 12/1994 | Bushnell ................................ 433/37 |
| 5,432,703 | 7/1995 | Clynch et al. . |
| 5,448,472 | 9/1995 | Mushabac . |
| 5,452,219 | 9/1995 | Dehoff et al. . |
| 5,513,985 * | 5/1996 | Robertson ............................... 433/37 |
| 5,549,476 | 8/1996 | Stern . |
| 5,636,985 * | 6/1997 | Simmen et al. ........................ 433/37 |
| 5,718,578 * | 2/1998 | Shimabukuro ......................... 433/37 |
| 5,733,118 * | 3/1998 | Pankuch et al. ....................... 433/37 |
| 5,938,445 * | 8/1999 | Kodama ................................. 433/37 |

\* cited by examiner

BUCCAL IMPRESSION REGISTRATION APPARATUS, AND METHOD OF USE

CROSS-REFERENCE TO RELATED APPLICATIONS

This is a continuation-in-part of application Ser. No. 08/789,918, filed on Jan. 28, 1997, abandoned, the entire disclosure of which is hereby incorporated by reference. This application further relates to application Ser. No. 09/312,417 titled "Scanning Apparatus Fixture For Holding Impression Trays", filed on May 14, 1999, and commonly owned by the Assignee of the present invention.

FIELD OF THE INVENTION

The present invention relates generally to the formation of dental impressions, and more particularly to a buccal, or bitewing, impression registration apparatus, and method of use therefore, to record a bite registration of a patient's teeth. More particularly still, the present invention may be used to record a bite registration of a patient's teeth by forming a dental impression thereof. The dental impression is then scanned by a scanner to provide an electronic record of the bite registration.

BACKGROUND OF THE INVENTION

Dental study casts are an integral part of a dentist's understanding of how a patient's teeth and bite function in a static relationship. This static relationship serves three important functions. The primary function is one of a diagnostic function for interpretation of any discrepancies or problems that exist within the bite relationship. The second function is educational. For example, the study casts provide better communication as a concrete model while helping the patient understand any discrepancies that may exist in the way their teeth function in that static relationship. Third, the dental study casts serve an important medical/legal function in defining the pre-existing static bite relationship prior to the performance of any work. This work can be defined either from an oral surgical standpoint, prosthetic standpoint or orthodontic/periodontal standpoint.

Significant complications are associated with study casts, however, since the casts need to be stored for an extended period (generally seven years). For example, the storage of the study casts requires large amounts of space in humidity controlled environments, as well as extensive laboratory procedures involving OSHA guidelines and space utilization for the study casts to be constructed. In addition, a significant amount of turn-around time is required for the curing process of the plastic study casts to occur. In light of these significant constraints as well as the importance associated with having an accurate recording of the pre-existing bite relationship, there arises a need for an apparatus (or system) and method in which electronic image data can be collected from an impression to circumvent the need for storage of physical study casts.

Prior to discussing a summary of the present invention, however, detailed discussions of the construction of a working model (study cast) of the teeth and other prior art devices will be presented.

As noted above, in order to study dental work to be performed on a patient's teeth, a working model of the teeth constructed of a plaster study cast is created. The plaster cast is based on a series of impressions taken to obtain the geometry of the teeth. To take an impression, alginate impression material is poured into a tray (i.e., an impression tray) which is then introduced into the patient's mouth for a period of time (typically one to two minutes). The impression material sets about the teeth and soft tissues forming a negative impression. The patient also bites into a soft material for registering a simultaneous imprint of the upper and lower set of teeth which records the relationship of the teeth in the upper and lower jaws respectively in three planes of space.

Once the impressions have set, they are sent to a lab to be processed into an upper and lower plaster study cast. The study casts are articulated together via the bite registration material to reproduce the bite of the patient. After construction, the study casts are returned to the dentist/orthodontist as a working study cast.

A serious drawback of this method is the number of labor intensive steps required to produce the study casts, the space and legal storage requirements of the study casts, and the inability to interface the study casts interactively with other diagnosis information (e.g., photographs and radiographs). Accordingly, if additional work is required, the cast fails in some way or is damaged, and/or the cast is lost, then an additional impression series must be taken. Therefore, there also exists a need in the art to develop a set of electronic data from the series of dental impressions wherein only a single impression need be taken for multiple interactive functions.

In the past, several devices have been designed for the electronic imaging of teeth. Also, other devices are known which utilize numerical data to create prototype devices. While known examples of such systems and devices follow, generally such systems do not provide the accuracy required for orthodontic work. Instead, such systems are generally useful only for crowns, fillings, etc.

U.S. Pat. No. 4,182,312 generally discloses a dental probe having a stylus which is connected through a rod to a three position transducer. Three signals are produced for indicating the position of the probe at any point to which the probe is applied. The transducers are mounted on an index tray which is adapted to be fastened to the jaw of the patient. Thus the patient's jaw becomes the origin against which all measurements are made. Contact between the tip of the stylus and the patient's tissue completes a circuit to turn on a recording mechanism which receives the transducer's outputs.

U.S. Pat. No. 4,611,288 generally discloses a method of automatically producing dental prostheses (e.g., crowns, inlays, dentures and the like) using an optical impression taken of the oral region with nontraumatic radiation. The reflected waves are transformed into numerical data which is used to operate a numerically controlled machine in the fabrication process.

U.S. Pat. No. 4,752,964 generally discloses an apparatus for producing, from an object having a three-dimensional shape, a shape equivalent or analogous to the three-dimensional shape. Here, light is irradiated to the object in an optical cutting plane. The light is picked up by an image pick-up device, and two-dimensional positions of the light are obtained in a direction perpendicular to the optical cutting plane to determine its three dimensional shape.

U.S. Pat. No. 4,935,635 generally discloses a three-dimensional point measuring system which includes a laser diode for projecting a triangulating beam at a surface to be mapped, with the beam scanned repeatedly across the surface. Photodetectors detect the position of the beam as reflected from the mapped surface, given by triangulation Z-axis or depth information. Correlation of a particular point with the position of the scanner along the scan line gives Y-axis information, or information in a width direction. The scanner and diode are mounted on a slide or platform device which moves perpendicularly to the Y axis in the direction in and out of the mouth, driven by a stepper motor, and the monitored position of the stepper motor is coordinated with the other information on each spot to yield X-axis information.

U.S. Pat. No. 5,198,877 generally discloses a method and apparatus for optically sampling numerous points on the surface of an object to remotely sense its shape utilizing two stages. The first stage employs a moveable non-contact scanner, which in normal operation sweeps a narrow beam of light across the object, illuminating a single point of the object at any given instant in time. The location of that point relative to the scanner is sensed by multiple linear photo-detector arrays behind lenses in the scanner. These sense the location by measuring the relative angular parallax of the point. The second stage employs multiple fixed but widely separated photoelectronic sensors to detect the locations of several light sources affixed to the scanner. Individual light sources are distinguished by time-multiplexing their on-off states. A coordinate computer calculates the absolute spatial positions where the scanner light beam is incident on the object to generate a computer model of the object.

U.S. Pat. No. 5,224,049 discloses a method for use in preparing a dental prosthesis and U.S. Pat. No. 5,347,454 generally discloses a system for use in preparing a dental prosthesis.

U.S. Pat. No. 5,448,472 discloses a method for collecting three-dimensional surface information in dental applications via a video camera. A tape strip is applied to a tooth surface to provide a distance reference or standard for use by a computer in analyzing the video data to determine actual distances. The tape strips are additionally provided with identification markings identifying the type of surfaces and the teeth to which the tape strips are attached.

Each of the foregoing systems, devices and methods suffer the drawback in that bulky, expensive specialized devices are required. The processes are extremely time consuming or require the introduction of devices into the patient's mouth for extended periods of time or which leads to patient discomfort. Also, these systems are limited to dental restorative procedures only. Reduced accuracy and precision of the measurements also greatly limit the usefulness of these systems to direct scanning of the dental impressions, study casts or both.

As mentioned previously, one previous method of recording the bite registration of the upper and lower sets of teeth is to place a soft member between the upper and lower sets of teeth. The patient them bites down into the soft member to record the bite registration. A drawback of this type of device for recording bite registration is that it prevents full closure of the teeth, thereby preventing a complete and fully accurate impression of the bite registration.

Therefore, there arises a need for a simplified apparatus and method for forming a dental impression to record the bite registration of a patient's teeth.

SUMMARY OF THE INVENTION

The present invention provides an improved apparatus and method for forming dental impressions to record the bite registration of a patient's teeth. In accordance with the present invention, an impression is taken of a predetermined set of teeth in the buccal region of the patient's mouth to record the bite registration of the upper and lower teeth. Therefore the use of an entire bite registration tray is eliminated, thereby reducing the amount of impression material that is used to record the bite registration. Furthermore, the apparatus of the invention allows complete bite registration of the upper and lower sets of teeth, since the apparatus is not placed between the patients teeth thereby allowing full closure of the upper and lower sets of teeth. Thus, the apparatus results in a more accurate impression. The partial dental impressions can then be scanned using a scanning system and method of the type described herein to electronically record the bite registration of the patient, so that visual displays, study casts, etc. can be created with the proper spatial relationships. The partial dental impressions can also be used to help create a plaster study cast of the patient's teeth, in a manner similar to that described above.

In a preferred embodiment of the apparatus according to the principles of the present invention, a buccal, or bitewing, impression apparatus includes a rigid frame member having first and second arms and a central section interconnected therebetween. The arms are spaced from each other and extend from the central section to an open, first end of the frame, thereby defining an open area between the arms and the central section. A mesh material is connected between the first and second arms and the central section within the open area. The mesh material permits a moldable material to adhere to the frame member during the formation of the impression, with the frame member supporting the moldable material and providing a means to support the impression upon the scanning apparatus. The buccal apparatus has a length such that it extends over a predetermined set of teeth on one side of the patient's mouth. In this manner, in order to establish the bite registration, only a partial impression is recorded.

The method in accordance with the principles of the present invention includes inserting a buccal impression apparatus into the patient's mouth, generally over the canine, first and second pre-molars, and first molar, of the upper and lower teeth on each side of the mouth. The buccal apparatus extend generally vertically with the open ends thereof directed toward the front of the mouth to facilitate injection of a moldable material. The moldable, impression material, such as alginate impression material, is then injected into the patient's mouth, between the predetermined set of teeth and each buccal apparatus, and allowed to set. It will be appreciated that when set, the material forms a negative impression of the outside surfaces of the predetermined set of teeth and surrounding soft tissues. The moldable material extends through and around the mesh material, such that the material adheres to each buccal apparatus upon setting. Thus, an impression is formed of each set of upper and lower teeth on both sides of the patient's mouth to record the bite registration of the patient. The thus formed impressions can then be scanned in the manner described herein to electronically record the bite registration.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying description, in which there is described a preferred embodiment of the invention.

BRIEF DESCRIPTION OF THE DRAWINGS

Referring to the drawings, wherein like numerals represent like parts throughout the several views.

DETAILED DESCRIPTION OF THE PREFERRED EMBODIMENT

A detailed discussion of the present invention will be deferred pending a discussion of a scanning method and the various preferred devices used in connection with the scanning apparatus and method.

1. Overview

Figure 1:
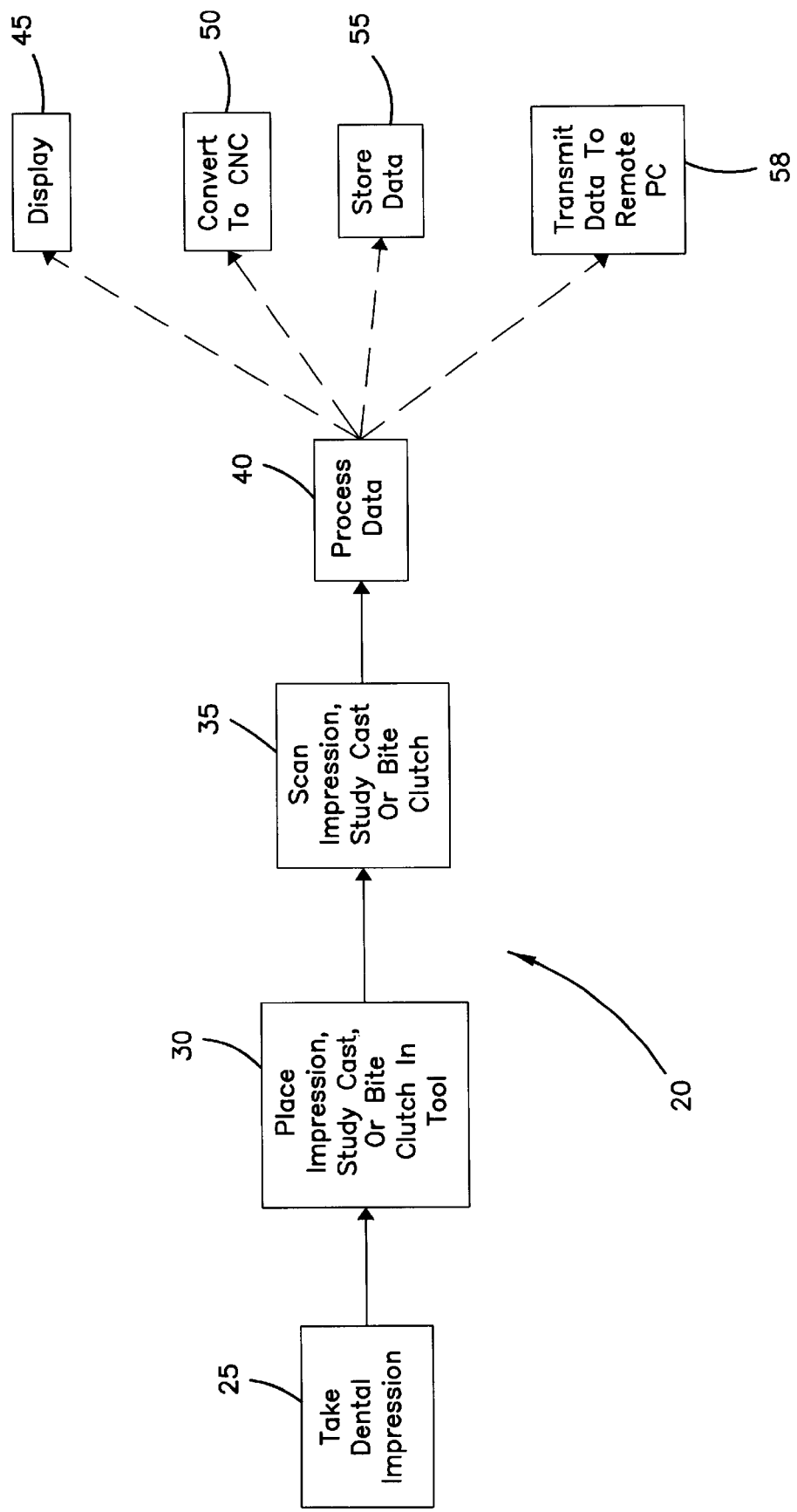
FIG. 1 illustrates the method steps 20 used in a scanning system and method of the present invention.
Figure 2A:
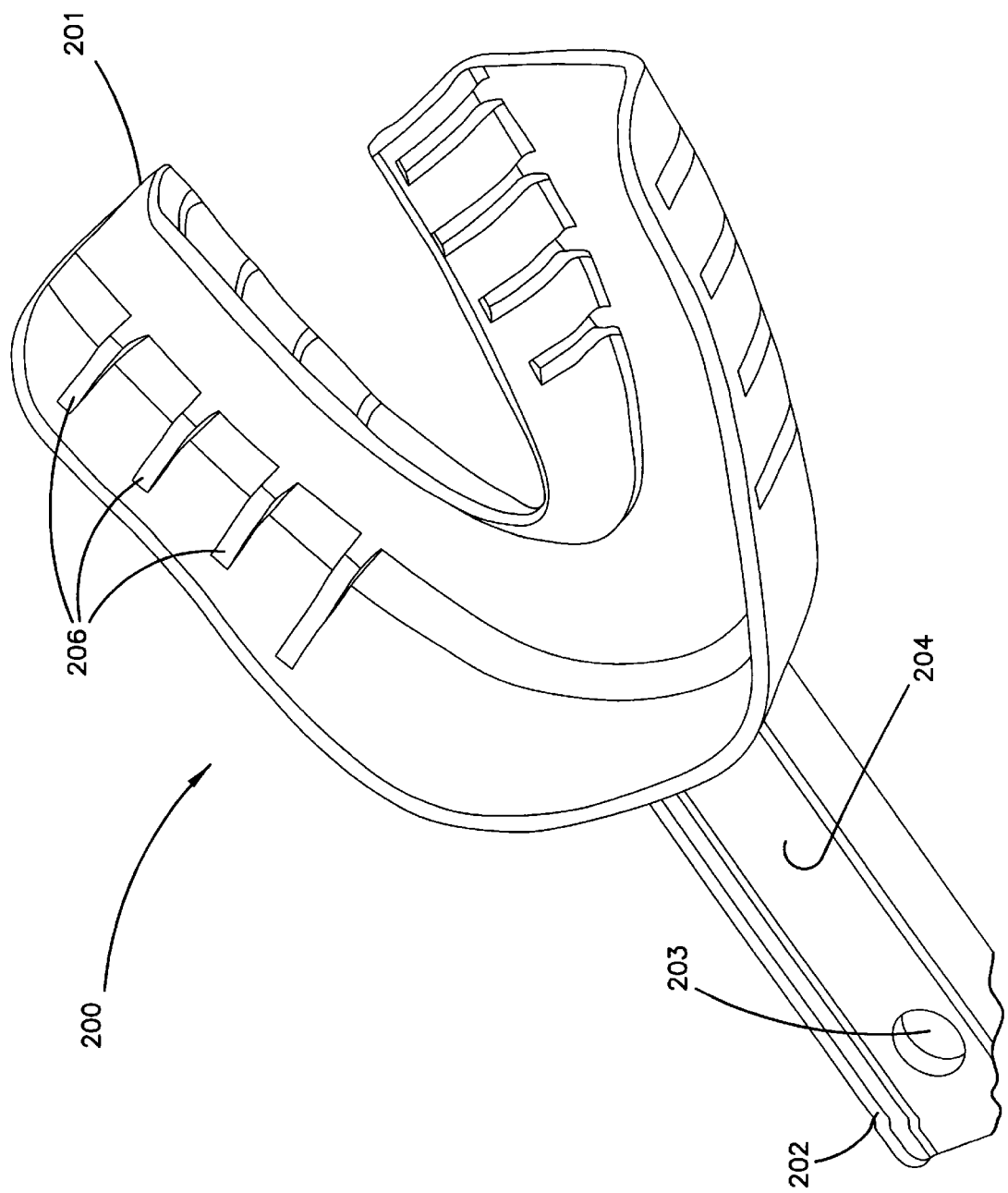
FIGS. 2a and 2b illustrate perspective views of lower 200 and upper 220 impression trays.
Figure 2B:
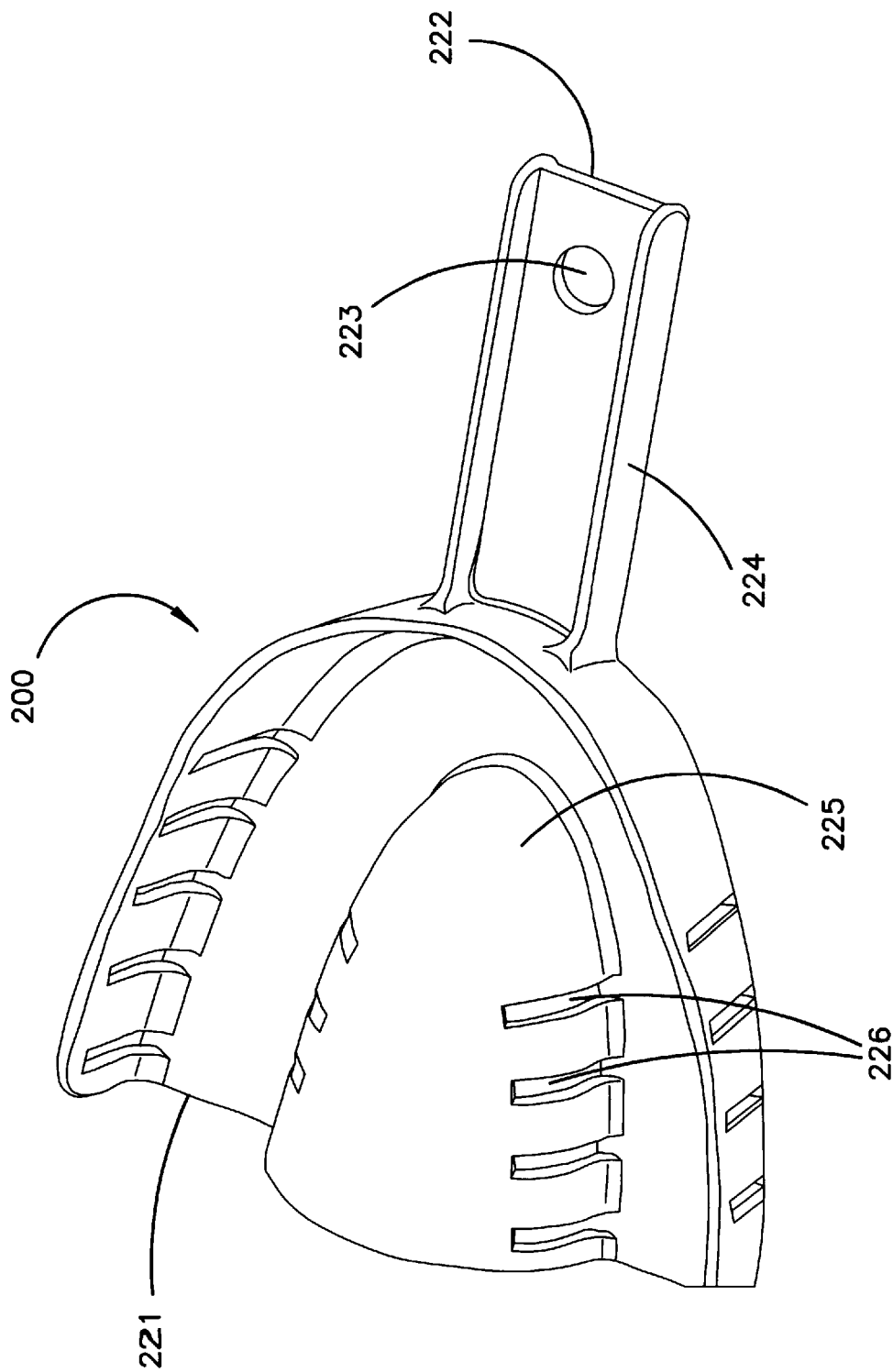

Referring first to FIG. 1, the overall method of the present invention is illustrated generally by the designation 20. First, at block 25, a dental impression of a patient's teeth and surrounding soft tissues (hereafter referred to collectively as "teeth" for convenience) is taken. The impression material hardens, forming a negative image of the teeth. The lower 200 and upper 220 trays used in connection with taking the impression are described below and are best seen in FIGS. 2a and 2b respectively. The bite/clutch tray 300 or the buccal impression apparatus 100 used in connection with determining the correct spatial orientation and relationship between the upper and lower impressions is described below and is best seen in FIGS. 3a and 3b, and FIGS. 7 and 8a–c.

At block 30, the impression tray 200 or 220 is placed in the tool or fixture 600 (described below and best seen in FIG. 5). The fixture 600 is used to securely hold the tray 200, 220, the tray 300, and/or the buccal apparatus 100 during the scanning step. The fixture 600 may also aid the scanning step by helping rotate the mold so that the image data can be properly generated. It will be appreciated that during this step at least one of the trays 200 and 220 include the hardened impression material which defines a negative image impression or mold of a patient's teeth.

Next at block 35, the scan of the impression occurs. In the preferred embodiment, a scanner manufactured by Laser Design Inc. of Minneapolis, Minn. designated as model number 8849648 may be used. The operation and scanning methodology used by this type of scanner is generally described in U.S. Pat. No. 5,124,524 (which is hereby incorporated herein by reference). Generally, this type of scanner is referred to as a line scanner device. It will be appreciated that for a complete study cast of the upper and lower teeth, two scans of the negative image impressions occur (i.e., one lower and one upper). Further, in order to properly reference the two sets of teeth together, a scan of the bite tray 300 or buccal 100 impression (best seen in FIGS. 7, 8a, 8c, and 8c) also takes place.

Figure 6:
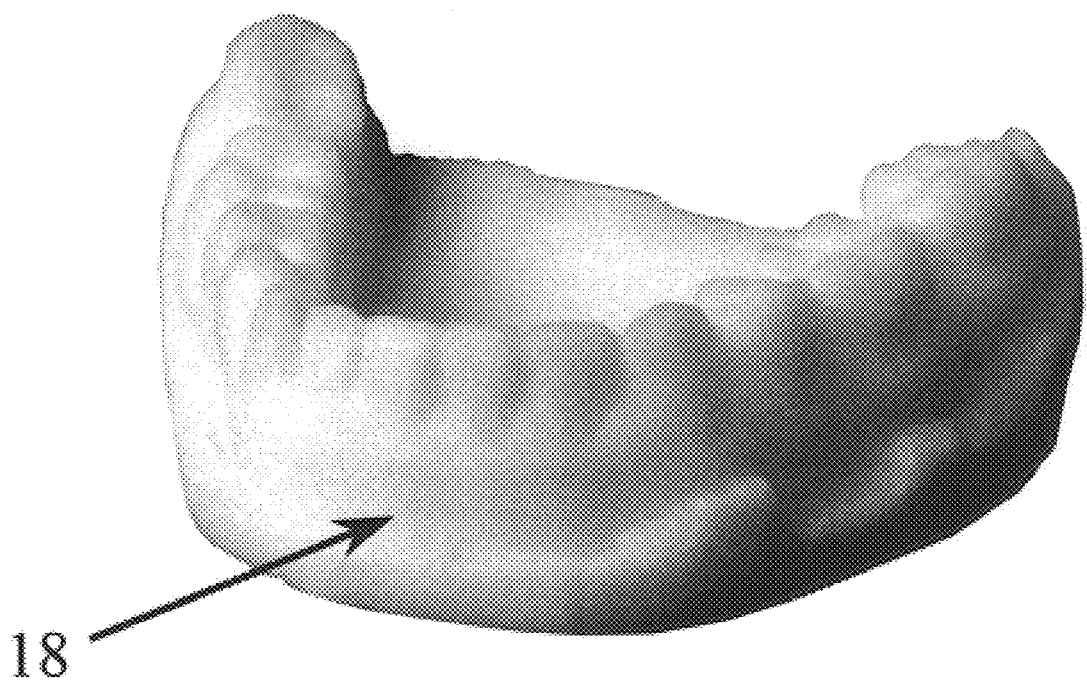
FIG. 6 is a perspective view of a positive image of a scanned portion of a study cast.

Referring now to FIGS. 1 and 6, at block 40 the image data is processed by processor 501. Such processing may include converting the negative image scan data into a positive image for display on a video display unit 503 (at optional block 45); converting the negative image scan data into CNC or other format of output for use by a fabrication device 507 (also known as a prototyping apparatus) (at optional block 50); storing the negative image scan data in a memory location or device 504 (at optional block 55); and/or transmitting the negative image scan data to a remote processor 505 via modem block 502 (at optional block 58).

In the preferred embodiment, one commercially available software package which may be used to generate three dimensional images from the line scan data is the package sold under the designation DataSculpt software available from Laser Design Inc. of Minneapolis, Minn.

2. Detailed Description of Components

Turning now to FIGS. 2a and 2b, the lower impression tray 200 and upper impression tray 220 are illustrated. The trays 200 and 220 are shown without impression material located thereon in order to more clearly illustrate the size and configuration of the respective trays. The trays 200 and 220 are generally horseshoe shaped with an elongate member 204 and 224 (respectively) integrally attached to and extending away from the arcuate portion of the horseshoe section. The elongate members 204 and 224 are generally within the same mean plane formed by the horseshoe section. However, those of skill in the art will appreciate that other locations and arrangements may be utilized. The upper tray 220 also includes a domed element 225 which is integrally formed and connects the interior portion of the horseshoe section of the tray 220.

Each of the trays 200 and 220 also includes a first end 201 and 221 (respectively) which is inserted into a patient's oral cavity during the process of taking the impression and a second end 202 and 222 (respectively) which includes a handle for helping insert and remove the trays. Located proximate the second ends 202 and 222 are holes 203 and 223 (respectively) which are arranged and configured to aid in the registration process of the scanning procedure (i.e., the holes 203 and 223 on the handles may be used in conjunction with the mounting fixture 600). However, including such holes 203 and 223 and/or using the holes in the registration process is optional.

Slots 206 and 226 are formed in the lower and upper trays 200 and 220 (respectively) to aid in the expansion of the impression material when a patient bites into the same, as well as helping retain the impression material on the tray 220 and 226 (and in a fixed manner) after removal from a patient's mouth and during scanning. Only several of the plurality of slots 206 and 226 are designated by the reference numerals in the Figures for the purpose of clarity. Also, those of skill in the art will appreciate that the number and arrangement of the slots 206 and 226 may be changed, with the slots 206 and 226 shown in FIGS. 2a and 2b being illustrative.

The trays 200 and 226 are preferably constructed by means of plastic injection molding process and of a material suitable for medical and dental purposes. Such material should also be selected to be rigid enough to hold the impression material in a stable fashion during scanning and be capable of being sanitized or sterilized.

Figure 3A:
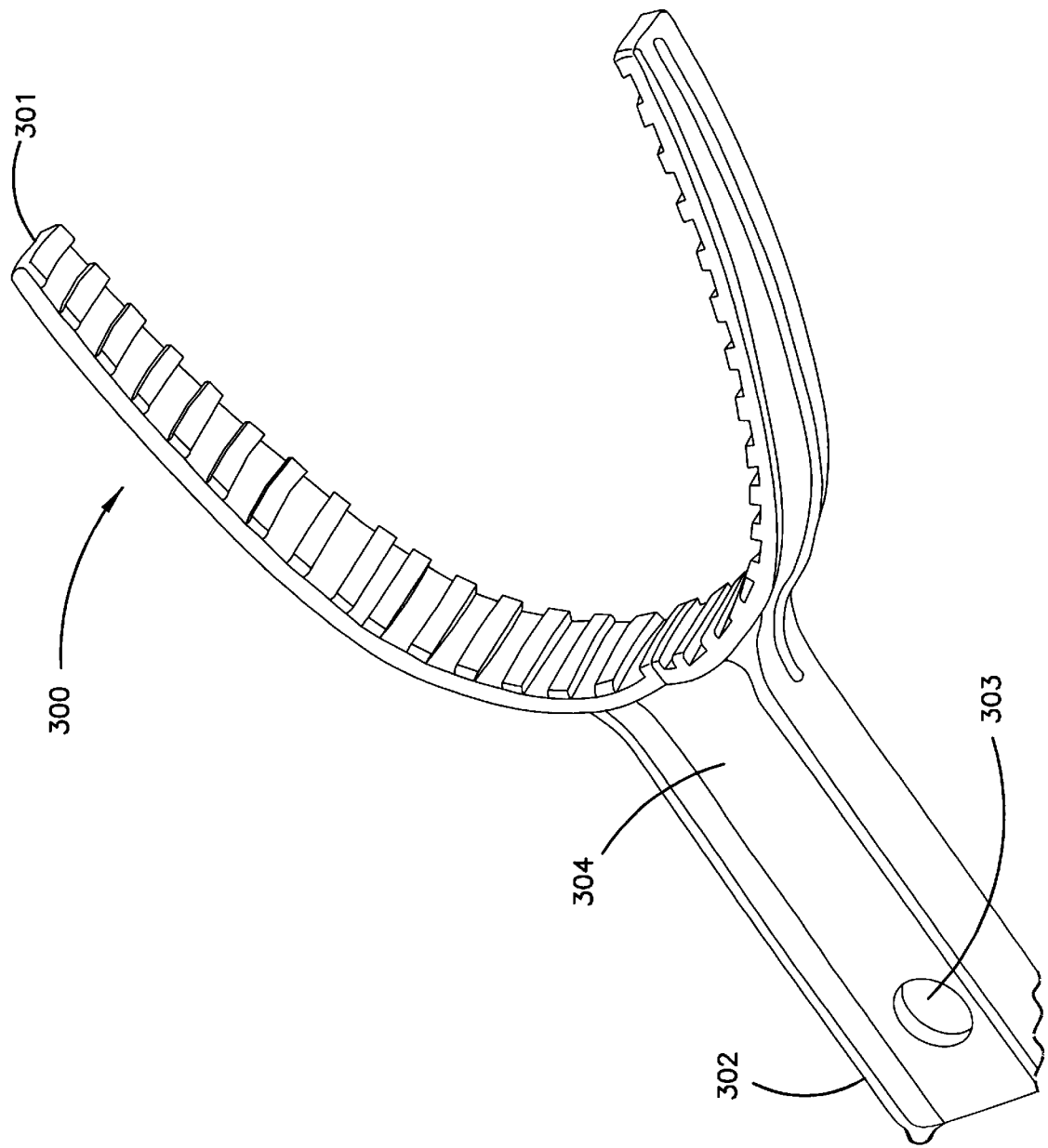
FIG. 3a illustrates a perspective view of a registration tray 300 used in connection with the present invention.
Figure 3B:
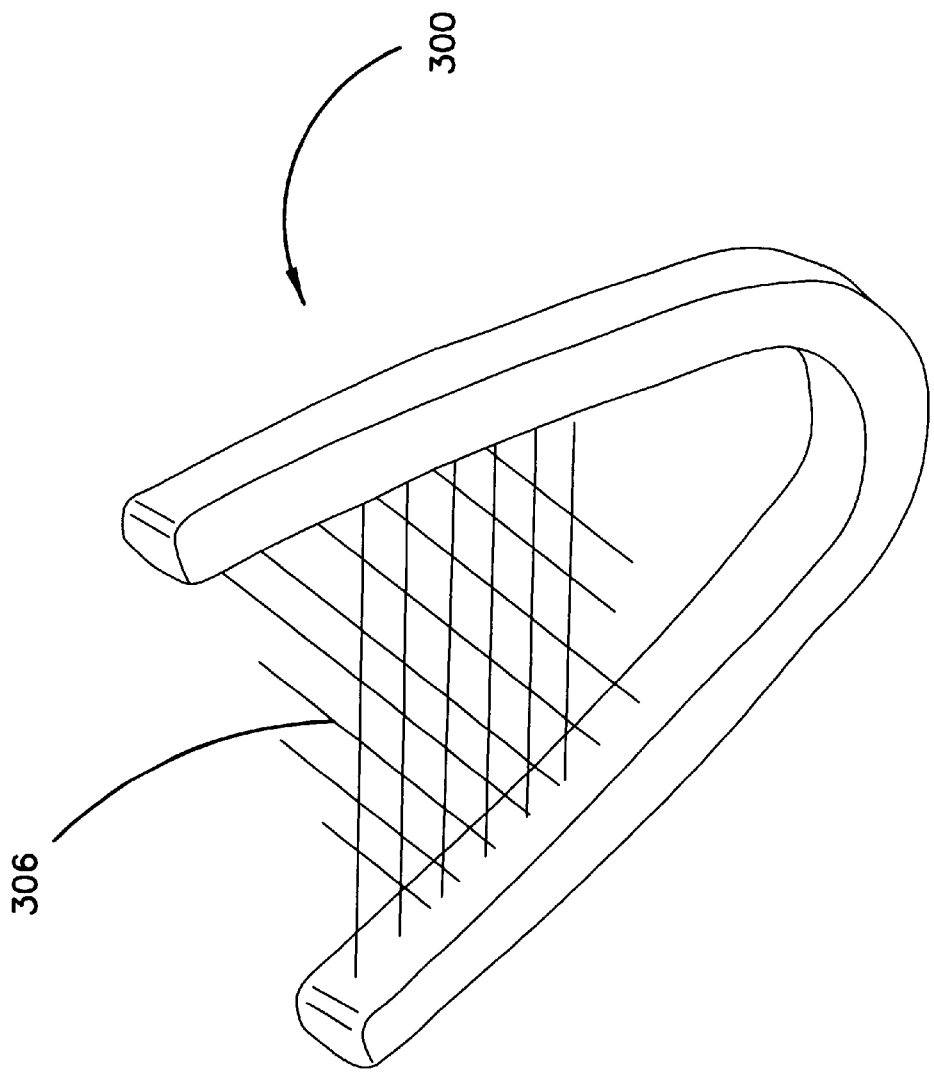
FIG. 3b diagrammatically illustrates the preferred arrangement and configuration of the impression material retaining mesh 306 used in connection with tray 300.

Turning now to FIGS. 3a and 3b, the bite registration tray 300 is illustrated. Tray 300 is shown without impression material located thereon in order to more clearly illustrate the size and configuration of the tray. The tray 300 is generally horseshoe shaped with an elongate member 304 integrally attached to and extending away from the arcuate portion of the horseshoe section generally in the same mean plane formed by the horseshoe section,.

Tray 300 includes a first end 301 which is inserted into a patient's oral cavity during the process of taking the impression and a second end 302 which includes a handle for helping insert and remove the tray 300. Located proximate the second end 302 is hole 303 which is arranged and configured to aid in the registration process of the scanning procedure (i.e., the holes on the handles may be used in conjunction with the mounting fixture 600). However, including such hole 303 and/or using the hole in the registration process is optional.

FIG. 3b illustrates the bite tray 300 without the elongate member 304 and including an impression retaining mesh material 306 generally located within the horseshoe section. The material 306 is used to retain the impression material on the tray. It will be appreciated that this configuration allows a patient to bite into the impression material on either side of the mean plane formed by the horseshoe portion of tray 300 to register the upper and lower impressions relative to one another so that study casts, visual displays, etc. can be created with the proper spatial relationships. In the preferred embodiment, tray 300 is constructed in a manner similar to that described above in connection with trays 200 and 220.

Figure 7:
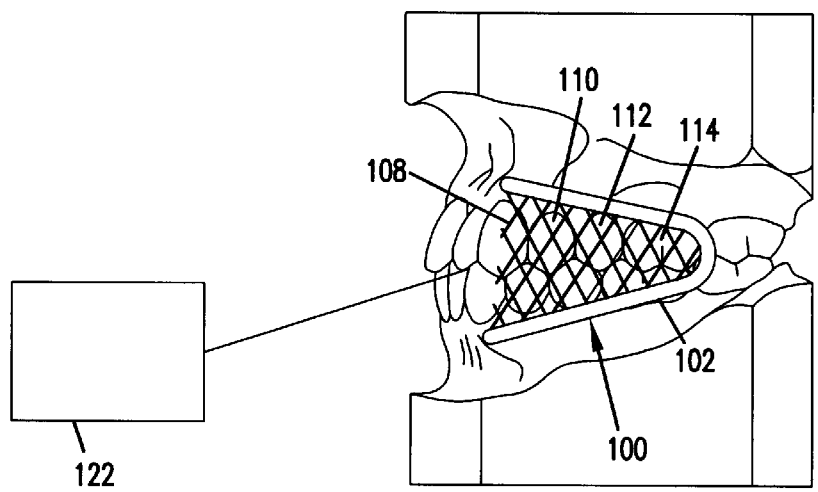
FIG. 7 is a side view of a set of teeth illustrating the location of a buccal impression registration apparatus relative to the teeth, with an injection apparatus to inject moldable material.

As an alternative to the bite tray 300, a buccal, or bitewing, apparatus 100 can be used to generate a partial impression of the patients teeth in order to record the bite registration. As illustrated in FIG. 7, the buccal apparatus 100 includes a rigid frame member 102 defining an open area with a mesh material 104 disposed within the open area of the frame. The frame 102 extends over only three edges of the apparatus 100 such that the frame includes an open end 106. The apparatus preferably has a length at least equal to the distance between the canine 108, first pre-molar 110, second pre-molar 112 and first molar 114 teeth of both the upper and lower sets of teeth, and extends from the upper gum to the lower gum when properly located within the patient's mouth in the buccal region thereof. However, the buccal apparatus 100 can be sized to meet the patients dentition based on the recommendations of the dentist, and thus the buccal apparatus 100 could be sized to extend over different ranges of teeth of the upper and lower sets of teeth.

As is apparent from FIG. 7, when the buccal apparatus is properly placed within the patient's mouth, the frame is oriented generally vertically between the patient's cheek and the outside surfaces of the teeth 108,110,112,114 and surrounding soft tissues, with the open end 106 directed toward the front of the patient's mouth. An identical apparatus 100 is similarly placed within the patient's mouth on the opposite side thereof to form an impression of the other set of teeth 108–114 and surrounding soft tissues on the other side of the mouth.

Figure 8A:
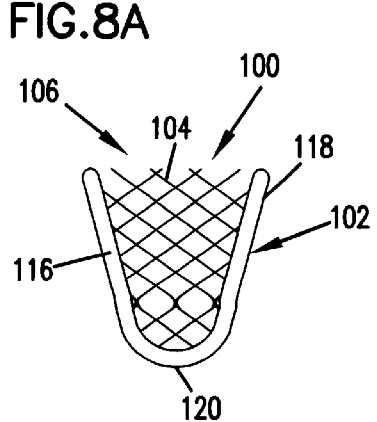
FIG. 8a illustrates one embodiment of the buccal apparatus.
Figure 8B:
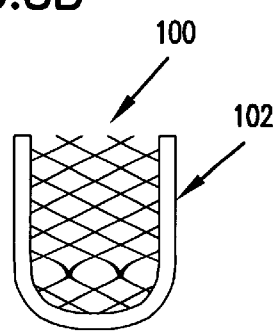
FIG. 8b illustrates a second embodiment of the buccal apparatus.
Figure 8C:
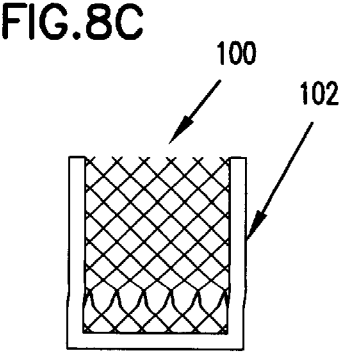
FIG. 8c illustrates a third embodiment of the buccal apparatus.

As illustrated in FIGS. 8a–c, the frame 102 can have various shapes. For instance, the frame can have a semi-elliptical or semi-oval shape (FIG. 8a), a U-shape (FIG. 8b), or a rectangular shape (FIG. 8c). In each instance, the frame includes first and second arms 116 and 118, respectively, with a central section 120 at one end of the frame interconnected between the arms. The arms 116,118 are spaced from each other at their free ends to define the open end 106 opposite the central section 120. The mesh material 104, which can be made of a plastic, metal wire or fabric material, is fastened to the frame such that it is disposed within the open area of the frame. The mesh material 104 is used to retain the impression material on the buccal apparatus. Further, the frame 102 is constructed such that it can be held by the fixture 600, and is sufficiently rigid so as to hold the impression material in a stable fashion during scanning. The frame 102 is preferably formed of plastic, metal or other rigid materials suitable for oral use. The material forming the frame and mesh should be capable of being sanitized or sterilized before scanning, as well as after removal of the impression material to allow re-use.

Figure 9:
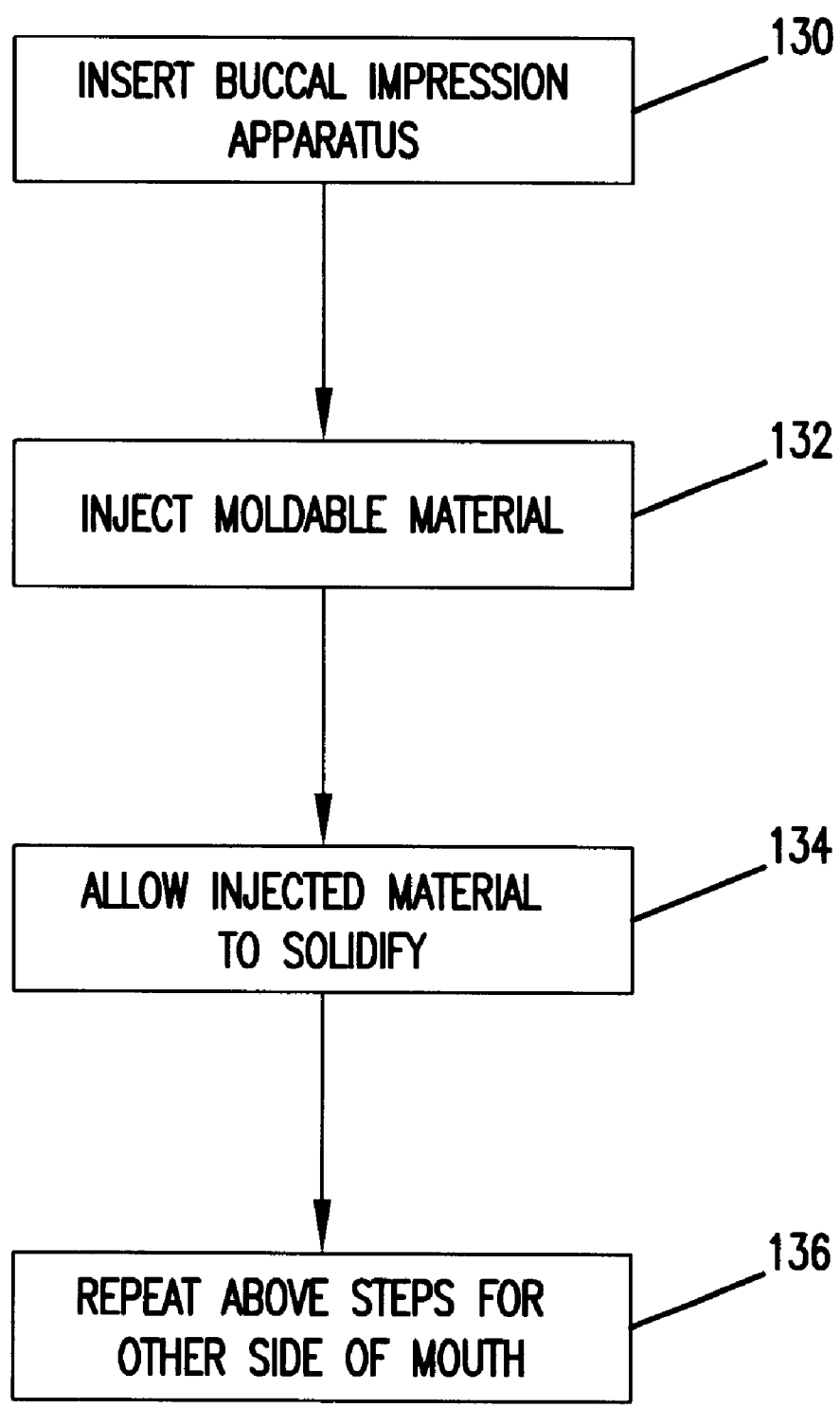
FIG. 9 illustrates the method steps used to form a buccal impression.

With reference to FIG. 9, the buccal apparatus 100 in use is inserted into the patient's mouth at step 130 generally over the teeth 108,110,112,114 and surrounding soft tissues, with the open end facing toward the front of the patient's mouth, in the manner illustrated in FIG. 7. With the patient taking a normal bite so that the teeth are arranged into the usual bite arrangement, a moldable impression material is injected between the buccal apparatus and the teeth at step 132, through the open end 106, so that the teeth and surrounding soft tissues are covered. Injection can be accomplished using an injection device 122, such as a syringe or the like, illustrated in FIG. 7. The moldable material is then allowed to set at step 134 (usually over a period of one to two minutes), thereby forming a negative impression of the arrangement of the teeth 108–114 and surrounding soft tissues. A portion of the injected material flows through and around the mesh material such that the material is firmly secured to the frame upon setting. In step 136, this process is repeated for the other set of teeth 108–114 on the opposite side of the mouth, either simultaneously with, or subsequent to, the formation of the impression of the first set of teeth.

The formed impressions are then mounted in the fixture 600 for subsequent scanning using the scanning system and method described herein to electronically record the bite registration of the patient. The impressions can also be used in a conventional plaster study cast system of the type described previously herein to record the relationship of the teeth in the upper and lower jaws. In contrast to previous bite registration apparatus in which a moldable material is disposed between the upper and lower dentitions to record the bite registration, the buccal apparatus 100 permits the bite registration of the upper and lower dentitions to be recorded when the upper and lower dentitions are in contact with each other. Therefore since no material is disposed between the upper and lower dentitions, a more accurate recording of the bite registration can be obtained. Further, by forming an impression of only a portion of the upper and lower dentitions, the surface area that needs to be scanned is reduced while still obtaining an accurate recording of the bite registration.

Figure 5:
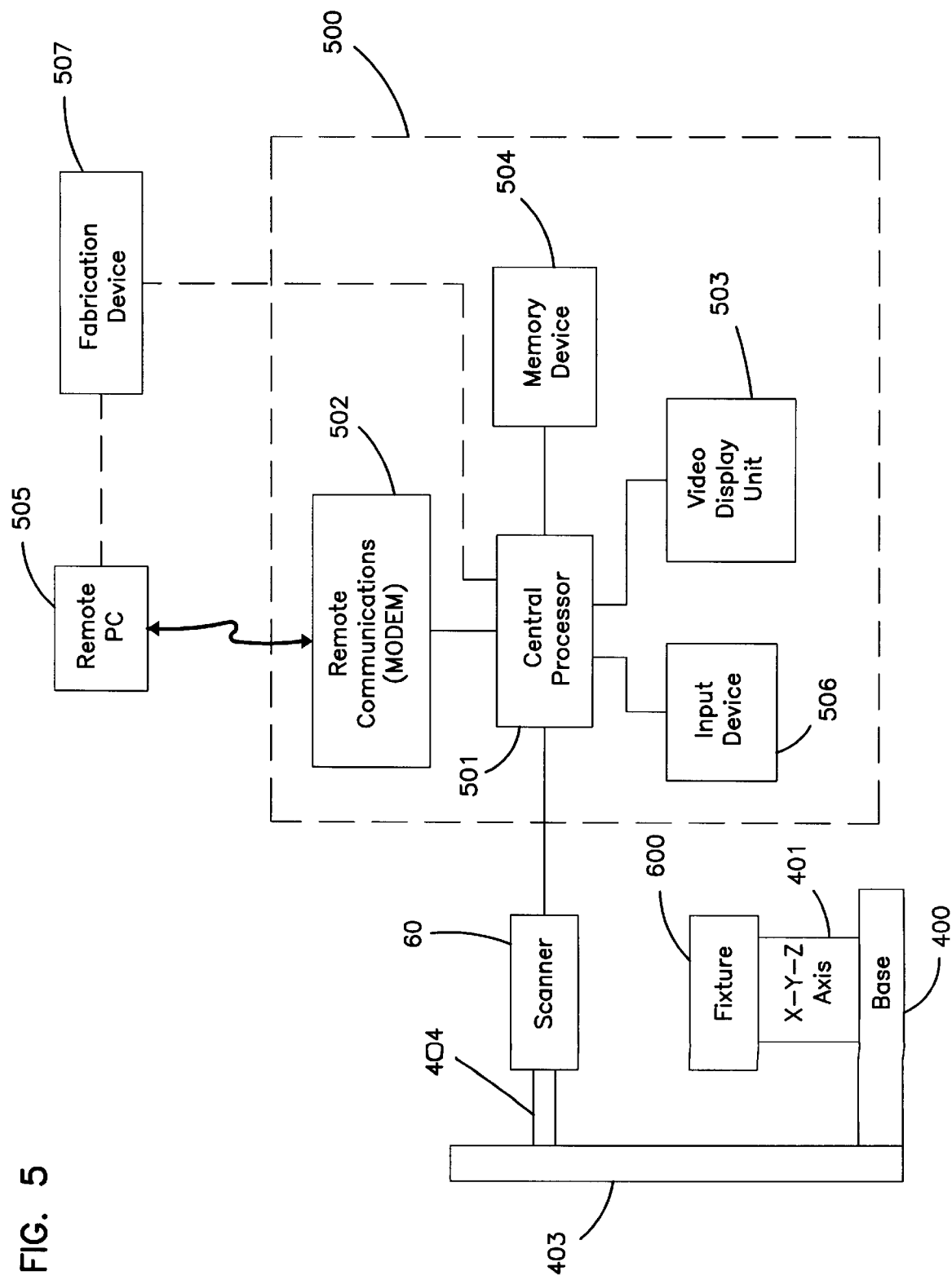
FIG. 5 diagrammatically illustrates the functional blocks associated with the processor, memory, and remote computer associated with processing the data from the scanner 60.

The scanning tool or fixture 600 is best seen in FIG. 5. In the preferred embodiment, the fixture 600 is arranged and configured to securely hold the trays 200, 220, the bite tray 300, and/or the buccal apparatus 100 while rotating and/or moving on the fixture platform 402 (best seen in 4) as the array of negative image electronic data from the negative impression(s) is being generated by the scanner 60.

Figure 4:
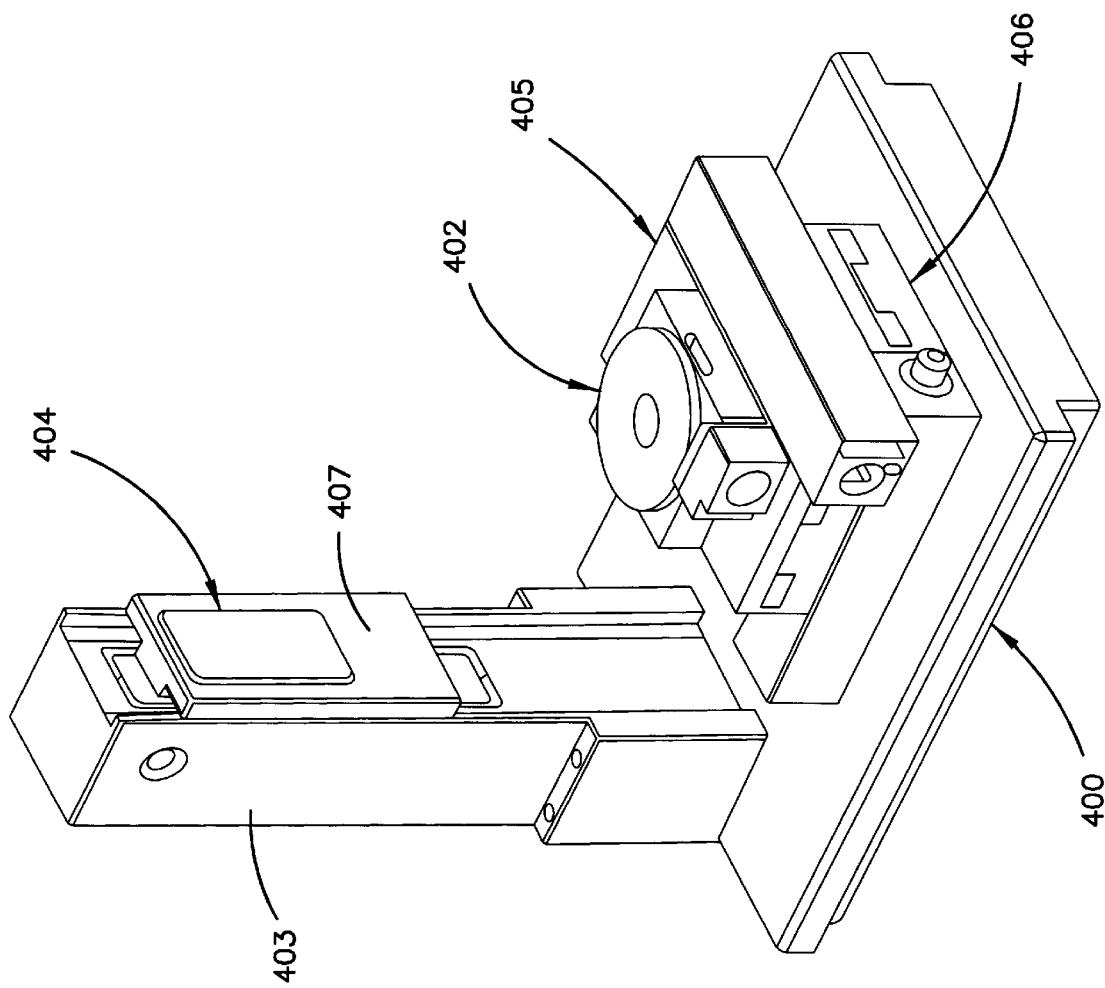
FIG. 4 illustrates a perspective view of a preferred embodiment base 400 and X-Y-Z axis devices 401 used in connection with scanner 60.

Referring to FIGS. 4 and 5, the scanner is designated generally at 60. As noted above, the scanner 60 and its operation is described in detail in U.S. Pat. No. 5,124,524. Also shown in FIG. 4 is the Z-axis column 407 which preferably provides precise vertical linear motion with a screw and nut assembly. Scanner mounting member 404 is operatively connected to the Z-axis column 407. Rotary stage 402 preferably provides precise rotational movement in the range of 0.001" quadrature resolution. X-axis stage 406 and Y-axis stage 405 provide X and Y coordinate control and preferably use lead screw assemblies. Column 403 is attached to base 400 and supports the scanner 60. In FIG. 5, the X axis stage 406, Y axis stage 405, the Z axis stage 407 and the rotational stage 402 are together referred to as block 401.

Still referring to FIG. 5, the functional blocks of the electronic components of the present invention are illustrated. The components include a computer 500 which preferably includes a processor 501, a video display unit 503, a memory device 504, a user input device 506 (e.g., a mouse and/or keypad), and a modem 502. Also illustrated is a remote computer 505, a fabrication device 507, and the scanner 60 (and its attendant X-Y-Z axis controllers and motors).

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and read-only memory devices. Further, the modem 502 is illustrated to show a communications capability. Such capability may also be by way of a network, etc.

Fabrication device 507 may be connected directly to the computer 500 or may be connected to a remote computer 505. The fabrication device 507 may be any number of devices which can utilize computer generated data and create a three-dimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM-1500.

In operation the array of negative image scan data is generated by the scanner 60 and provided to the processor 501. The negative image scan data may be saved in a memory device 504 as a permanent record of the baseline condition of the patient's teeth, or temporarily prior to one of several other options. For example, the data may be converted to a positive image and stored in that fashion as a permanent record of the baseline condition. Alternatively, the positive image may be displayed on the video display unit 503 for teaching or educational purposes with the patient. Still further, the positive information data may be transmitted to a remote PC 505 for storage, study by a consulting dentist (or physician), or fabrication of a study cast by fabrication device 507. The fabrication device 507 may optionally be connected directly to computer 500. These and other options may be selected by the computer 500 user via the input device 506.

The programming operation of the processor 501 provides for scanning each of the upper and lower impressions and the bite registration impressions. These scans provide the information necessary to create an electronic equivalent of the prior art physical study casts. By using negative image impressions and a line scanner, high resolution and speed are gained wherein high quality study casts may be generated by a fabrication device 507 thereby replacing older methods of constructing the same. Although such fabricated casts may still be saved, since the data is generated and stored electronically, the problems associated with storage of prior art study casts may be reduced and/or eliminated. Further, the data may be used any number of times in different ways to accomplish a more robust practice.

It will be appreciated that the principles of this invention apply not only to the devices used to implement the invention, but also the method in general of generating an electronic array of dental impression scan image data from one or more negative impressions. For example, it is possible to scan existing study casts in order to generate an electronic data set and view the set in three dimensions as seen in FIG. 6 at the designation 18. By doing so, the image may be manipulated and/or stored as described above. Further, by doing so, the requirement to store existing study casts may be reduced or eliminated.

It is also contemplated that other impressions of a patient's body may be taken to form a negative image mold. The present invention may also be used to scan such negative images. A further extension of the present invention is to generate a direct scan image of teeth in a patient's oral cavity with a tool inserted in a patients mouth and provided to central processor 501.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A buccal impression registration apparatus comprising:
   a frame including first and second equal length arms and a central section interconnected therebetween, said arms being spaced from each other and extending from said central section to a first end of the frame to thereby define an open area between the arms and the central section;
   a mesh material connected between the first and second arms and the central section substantially within the open area;
   wherein the buccal impression registration apparatus is generally planar to permit the apparatus to be inserted between outer surfaces of a patient's teeth and the patient's check.

2. The buccal impression apparatus according to claim 1, wherein the arms are not connected to each other at the first end such that the first end of the frame is open.

3. The buccal impression apparatus according to claim 2, wherein the mesh material at the first end of the frame extends along a generally continuous linear line between the ends of the first and second arms.

4. The buccal impression apparatus according to claim 3, wherein the mesh material at the first end of the frame is unsupported between the ends of the first and second arms.

5. The buccal impression registration apparatus according to claim 1, wherein the buccal impression registration apparatus is symmetrical on either side of an axis that bisects the apparatus through the central section.

6. The buccal impression apparatus according to claim 1, wherein the frame has a length sufficient to extend over a predetermined plurality of teeth.

7. The buccal impression apparatus according to claim 6, wherein the length of the frame is at least equal to the distance between a canine and a first molar tooth.

8. The buccal impression apparatus according to claim 6, wherein the length of the frame is approximately equal to the distance between a canine and a first molar tooth.

9. The buccal impression apparatus according to claim 1, wherein the frame is rigid and the mesh material is located entirely within the open area.

10. A method of forming a dental impression to record a bite registration of upper and lower sets of teeth, comprising:
    a) inserting a buccal impression registration apparatus between a patient's cheek and outer surfaces of a predetermined set of teeth of the upper and lower sets of teeth, with no portion of the apparatus disposed between the upper and lower sets of teeth;
    b) injecting a moldable material between the buccal impression registration apparatus and the outer surfaces of the predetermined set of teeth of the upper and lower sets of teeth; and
    c) allowing the injected moldable material to at least partially solidify and thereby form an impression of the predetermined set of teeth of the upper and lower sets of teeth.

11. The method according to claim 10, wherein the step of inserting the buccal impression registration apparatus comprises inserting the apparatus over the outer surfaces of canine, first premolar, second premolar, and first molar teeth of the upper and lower sets of teeth.

12. The method according to claim 11, wherein one end of the apparatus is disposed proximate the canine teeth, and an opposite end of the apparatus is disposed proximate the first molar teeth.

13. The method according to claim 11, further including forming the buccal impression registration apparatus to include a rigid frame having first and second arms and a central section interconnected therebetween, said arms being spaced from each other and extending from said central section to a first end of the frame to thereby define an open area between the arms and the central section, and the step of inserting comprises inserting the apparatus such that the first end of the frame extends toward the patient's mouth.

14. The method according to claim 11, further comprising inserting the buccal impression registration apparatus such that it extends generally vertically within the patient's mouth.

15. The method according to claim 13, further including forming the frame to include an open end, and wherein the step of inserting comprises inserting the apparatus such that the open end of the frame extends toward the patient's mouth.

16. The method according to claim 13, further comprising connecting a mesh material between the first and second arms and the central section within the open area, and wherein the moldable material extends through and around the mesh material whereby the moldable material is secured to the frame.

17. The method according to claim 10, further comprising inserting an additional said buccal impression registration apparatus between a patient's cheek and outer surfaces of a second predetermined set of teeth of the upper and lower sets of teeth in the opposite side of the patient's mouth, and repeating steps b) and c) for said additional buccal impression registration apparatus.

* * * * *

UNITED STATES PATENT AND TRADEMARK OFFICE
CERTIFICATE OF CORRECTION

PATENT NO. : 6,206,693 B1
DATED : March 27, 2001
INVENTOR(S) : Hultgren

It is certified that error appears in the above-identified patent and that said Letters Patent is hereby corrected as shown below:

Drawings,
Sheet 3 of 10: "200" should read -- 220 -- as shown below:

FIG. 2B

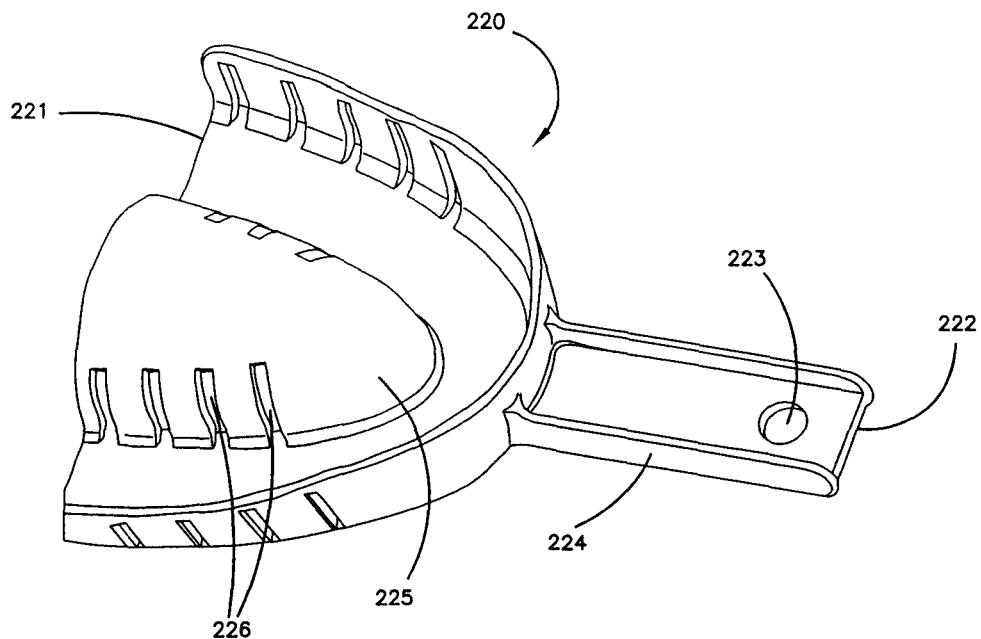

UNITED STATES PATENT AND TRADEMARK OFFICE
CERTIFICATE OF CORRECTION

PATENT NO.    : 6,206,693 B1
DATED         : March 27, 2001
INVENTOR(S)   : Hultgren It is certified that error appears in the above-identified patent and that said Letters Patent is hereby corrected as shown below:

Column 6,
Line 14, "FIGS. 7, 8a, 8c, and 8c)" should read -- FIGS. 7, 8a, 8b and 8c) --
Lines 62-63, "tray 220 and 226" should read -- tray 200 and 220 --

Column 7,
Line 4, "226" should read -- 220 --

Column 12,
Line 16, "The method according to claim 11, further comprising inserting the buccal impression registration apparatus such that it extends generally vertically within the patient's mouth." should read -- The method according to claim 11, wherein the frame generally defines a plane, and further comprising inserting the buccal impression registration apparatus such that the plane defined by the frame is oriented generally vertically within the patient's mouth. --

Signed and Sealed this

Thirtieth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

Page 1 of 2

PATENT NO. : 6,206,693 B1
APPLICATION NO. : 09/311436
DATED : March 27, 2001
INVENTOR(S) : Hultgren It is certified that error appears in the above-identified patent and that said Letters Patent is hereby corrected as shown below:

Title page (63), Related U.S. Application Data: "Jan. 28, 1997, now abandoned." should read --Jan. 28, 1997, now U.S. Patent No. 6,217,334.--

Drawings,
Sheet 3 of 10: "200" should read --220-- as shown below:

FIG. 2B

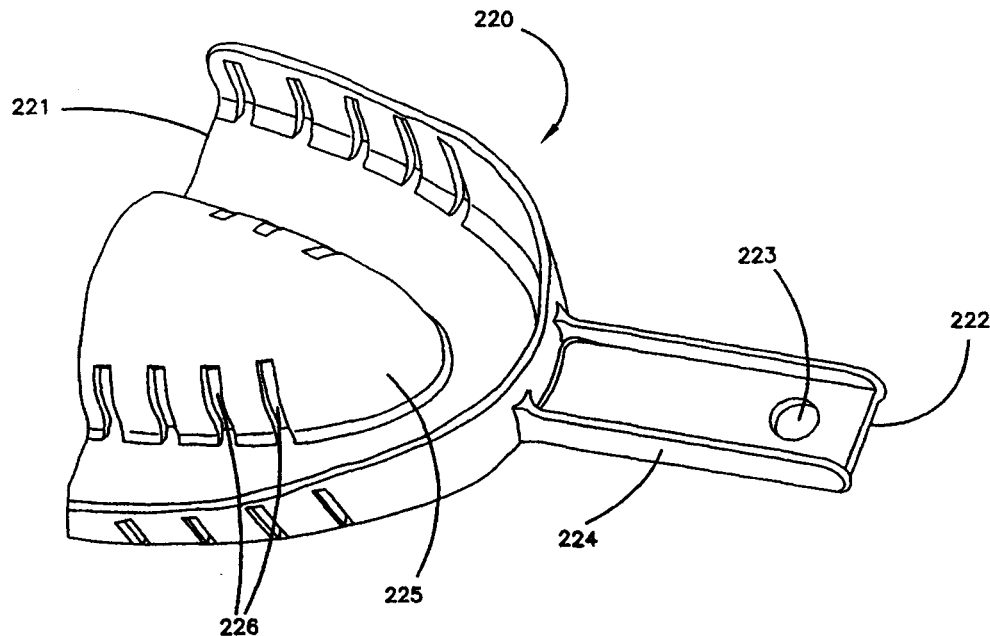

Col. 1, line 8: "Jan. 28, 2007, abandoned," should read --Jan. 28, 1997, now U.S. Patent No. 6,217,334,--

Signed and Sealed this
Twentieth Day of September, 2011

David J. Kappos
*Director of the United States Patent and Trademark Office*

CERTIFICATE OF CORRECTION (continued)
U.S. Pat. No. 6,206,693 B1

Column 6,
Line 14, "FIGS. 7, 8a, 8c, and 8c)" should read --FIGS. 7, 8a, 8b and 8c)--
Lines 62-63, "tray 220 and 226" should read --tray 200 and 220--

Column 7,
Line 4, "226" should read --220--

Column 12,
Line 16, "The method according to claim 11, further comprising inserting the buccal impression registration apparatus such that it extends generally vertically within the patient's mouth." should read --The method according to claim 11, wherein the frame generally defines a plane, and further comprising inserting the buccal impression registration apparatus such that the plane defined by the frame is oriented generally vertically within the patient's mouth.--